(12) United States Patent
Xing et al.

(10) Patent No.: US 11,639,512 B2
(45) Date of Patent: May 2, 2023

(54) CORYNEBACTERIUM CONSTITUTIVE EXPRESSION VECTOR PROMOTER SCREENED ON THE BASIS OF TRANSCRIPTOME SEQUENCING, SCREENING METHOD THEREOF, AND APPLICATIONS THEREOF

(71) Applicant: WUHAN GRAND HOYO CO., LTD., Wuhan (CN)

(72) Inventors: Panpan Xing, Wuhan (CN); Haixia Su, Wuhan (CN); Jiong Wang, Wuhan (CN); Xuechen Mei, Wuhan (CN); Kun Wan, Wuhan (CN); Mengjun Song, Wuhan (CN); Jing Li, Wuhan (CN); Aifu Liu, Wuhan (CN)

( * ) Notice: Subject to any disclaimer, the term of this patent is extended or adjusted under 35 U.S.C. 154(b) by 757 days.

(21) Appl. No.: 16/496,496

(22) PCT Filed: Mar. 14, 2018

(86) PCT No.: PCT/CN2018/079034
§ 371 (c)(1),
(2) Date: Sep. 23, 2019

(87) PCT Pub. No.: WO2018/171488
PCT Pub. Date: Sep. 27, 2018

(65) Prior Publication Data
US 2020/0024625 A1 Jan. 23, 2020

(30) Foreign Application Priority Data

Mar. 21, 2017 (CN) .......................... 201710169454.5
Mar. 21, 2017 (CN) .......................... 201710169685.6
Mar. 21, 2017 (CN) .......................... 201710169693.0

(51) Int. Cl.
| | |
|---|---|
| C12P 13/06 | (2006.01) |
| C12N 1/20 | (2006.01) |
| C12N 15/77 | (2006.01) |
| C12N 15/113 | (2010.01) |
| C12Q 1/02 | (2006.01) |
| C12R 1/15 | (2006.01) |
| C12Q 1/6897 | (2018.01) |

(52) U.S. Cl.
CPC ............... *C12P 13/06* (2013.01); *C12N 1/20* (2013.01); *C12N 1/205* (2021.05); *C12N 15/113* (2013.01); *C12N 15/77* (2013.01); *C12Q 1/02* (2013.01); *C12N 2800/101* (2013.01); *C12N 2800/24* (2013.01); *C12N 2800/60* (2013.01); *C12Q 1/6897* (2013.01); *C12R 2001/15* (2021.05)

(58) Field of Classification Search
CPC ...... C12N 15/1086; C12N 9/88; C12N 1/205; C12K 14/34
See application file for complete search history.

(56) References Cited

U.S. PATENT DOCUMENTS 6,107,063 A 8/2000 Moeckel et al.

FOREIGN PATENT DOCUMENTS

| CN | 101698845 A | 4/2010 |
|---|---|---|
| CN | 101838663 A | 9/2010 |
| CN | 101985631 A | 3/2011 |
| CN | 103820486 A | 5/2014 |
| CN | 103834679 A | 6/2014 |
| CN | 106434732 A | 2/2017 |
| CN | 107164369 A | 9/2017 |
| CN | 107164370 A | 9/2017 |
| CN | 107164371 A | 9/2017 |

OTHER PUBLICATIONS

Extended European search report issued in the counterpart European application No. 18772338.2, dated Oct. 22, 2020.
Marc Jakoby et al., "Nitrogen regulation in Corynebacterium glutamicum: Isolation of genes involved and biochemical characterization of corresponding proteins", FEMS Microbiology letters, pp. pages 303-310, Apr. 5, 1999, vol. 173, No. 2.
"Corynebacterium glutamicum amtP, glnB, glnD genes and partial ftsY and srp genes", EMBL Accession No. AJ010319, nts 557-696, Mar. 23,1999.
Supplementary Partial European Search Report issued in European Application No. 18772338.2, dated Jun. 3, 2020.
Joo-Young Lee et al. "Corynebacterium glutamicum whcB, a stationary phase-specific regulatory gene," FEMS microbiology letters, Feb. 1, 2012, pp. 103-109, vol. 327, No. 2.
Christof Larisch et al., "The alternative sigma factor SigB of Corynebacterium glutamicum modulates global gene expression during transition from exponential growth to stationary phase," BMC genomics, Jan. 4, 2007, vol. 8, No. 4.
Miroslav Pátek et al. "Corynebacterium glutamicum promoters: a practical approach", Microbial Biotechnology, Mar. 1, 2013, pp. 103-117, vol. 6, No. 2.
Liebl, W. et al., "Transfer of Brevibacterium divaricatum DSM 20297T, 'Brevibacterium flavum' DSM 20411, 'Brevibacterium lactofermentum' DSM 20412 and DSM 1412, and Corynebacterium lilium DSM 20137T to Corynebacterium glutamicum and their distinction by rRNA gene restriction patterns", International Journal of Systematic and Evolutionary Microbiology, 1991, vol. 41, No. 2, p. 255-260.
Brabeiz, W. et al., "Studies on the utilization of lactose by Corynebacterium glutamicum, bearing the lactose operon of *Escherichia coli*", 1991, Arch Microbiol, vol. 155, p. 607-612.

(Continued)

*Primary Examiner* — Tekchand Saidha
(74) *Attorney, Agent, or Firm* — Piloff Passino & Cosenza LLP; Sean A. Passino; Rachel K. Pilloff

(57) ABSTRACT

Provided is a method for screening a *Corynebacterium* constitutive expression vector promoter on the basis of transcriptome sequencing; and further provided are the *Corynebacterium* constitutive expression vector promoter screened on the basis of transcriptome sequencing, an expression vector comprising the promoter, a recombination strain obtained by transforming a host cell *Corynebacterium glutamicum* using the expression vector, and applications thereof.

20 Claims, 3 Drawing Sheets

Specification includes a Sequence Listing.

(56) References Cited

OTHER PUBLICATIONS

Jensen, PR et al., "Artificial promoters for metabolic optimization", Biotechnology and Bioengineering, 1998, vol. 58, Nos. 283, p. 191-195.

Yang, Liu et al., "Effects of promoter modification on xylose isomerase gene xylA expression in Ccumorynebacterium glutamin". Advances in New and Renewable Energy, 2014, vol. 5, No. 2, p. 353-357(with English abstract).

Yu, Xiaoxiao et al., "Research progress of Bacillus subtilis expresion system and its promoter regulatory elements", Biotechnoogy Bulletin, 2015, vol. 31, No. 2, p. 35-44 (with English abstract).

Chen, Xiaoxue et al., "Analysis of Regulatory Intensity of Inducible Promoters in Corynebacterium glutamicum ATCC13032", Journal of Shenyang Pharmaceutical University, 2017, vol. 34, No. 2, p. 169-175 (with English abstract).

GenBank Acession No. CP018175 GenBank Database 201, 2017, see the sequence and the related information.

First Office Action and Search Report issued in the Chinese priority application No. CN 201710169454.5 dated Jun. 21, 2019.

First Office Action and Search Report issued in the Chinese priority application No. CN 201710169685.6 dated Jun. 21, 2019.

First Office Action and Search Report issued in the Chinese priority application No. CN 201710169693.0 dated Jun. 17, 2019.

International Search Report and Written Opinion of PCT/CN2018/079034 dated Jun. 22, 2018.

Liu, Xiuxiao et al., "Selection of endogenous expression elements from Corynebacterium glutamicum", Microbiology China (with English abstract).

CORYNEBACTERIUM CONSTITUTIVE EXPRESSION VECTOR PROMOTER SCREENED ON THE BASIS OF TRANSCRIPTOME SEQUENCING, SCREENING METHOD THEREOF, AND APPLICATIONS THEREOF

The present application claims priority to Chinese patent applications CN201710169454.5, CN201710169685.6, and CN201710169693.0, filed on Mar. 21, 2017, which are incorporated herein by reference in their entirety.

FIELD OF INVENTION

The present invention belongs to the field of biotechnology, and particularly relates to a *Corynebacterium* constitutive expression vector promoter screened on the basis of transcriptome sequencing screening, a screening method thereof and applications thereof. The present invention further relates to an expression vector and a recombinant strain containing the promoter.

PRIOR ARTS

*Corynebacterium* is a kind of Gram-positive bacteria. *Corynebacterium glutamicum*, *Brevibacterium flavum* and *Brevibacterium lactofermentum*, three main representatives of *Corynebacterium*, have been widely used in the production of amino acids, nucleotides and other chemicals (Liebl et al., 1991). The *Corynebacterium* mutant strains obtained by physical or chemical mutagenesis have a strong ability to synthesize useful substances of interest, while wild or mutant strains of *Corynebacterium* can be modified by genetic engineering and metabolic engineering to obtain strains with higher production intensity. Metabolic engineering is to find key metabolic enzymes in various metabolic pathways of *Corynebacterium*, and regulate gene expression of key metabolic enzymes through genetic engineering. Usually genes are expressed under the control of a promoter, and their expression intensity depends on promoter elements. The promoters derived from *Escherichia coli*, *Streptomyces* and *Bacillus subtilis* can be expressed in *Corynebacterium* and can be applied to the construction of a vector system of *Corynebacterium*, such as expression plasmids PXMJ19 and PEC-XK99E constructed by using Ptac and Ptrc promoters derived from *Escherichia coli*. Genes are induced and expressed under the control of lacIq, but the expression level is low, and an inducer IPTG is needed in the production process while IPTG is quite expensive which is not a suitable inducer for gene expression in large-scale production of the target product. Lactose can be used as an inducer for large-scale production instead of IPTG, however, lactose cannot enter cells of most *Corynebacterium* strains (Brabetz et al., 1991), which also limits the application of inducible expression systems in *Corynebacterium*.

The constitutive promoter can continuously express foreign gene without special conditions such as induction during the survival period of the bacteria, thereby simplifying the operation process and having relatively high safety, and thus being more suitable for the application in actual production. The constitutive genes with strong expression were screened and purified by means of PCR amplification and DNA probes in various housekeeping genes, and constitutive strong promoters were screened for the construction of recombinant vectors (Jensen P R et al., Appl Environ Microbiol, 1998, 64(1): 82-87.). Yangliu et al. used Pgro, the endogenous strong promoter of *C. glutamicum* ATCC 13032, to effectively promote the expression of the exogenous gene xylA in *C. glutamicum* ATCC 13032 (Yang Liu et al., Progress in New Energy, 2014, 5(2): 353-357). Wang Xiaoyuan et al. obtained tac-M promoters with transcriptional initiation function by mutation, and constructed a constitutive expression vector PDXW-10, which express foreign proteins with moderate level in *Corynebacterium* (CN: 200910210962.9). Although the expression of the constitutive promoter has many advantages, the current screening method of which is complicated, and an urgent problem to be solved in industrial production is how to select a appropriate promoter for regulation to avoid the host cell growth stagnation or metabolic disorder, or the depletion of the host energy and the loss of the plasmid due to excessive protein expression. Currently, for instance, Pgro is used as a promoter to construct an expression plasmid together with the gene of interest. These kinds of plasmids also express the target gene in the logarithmic growth phase of bacteria, resulting in a loss rate of the plasmid reaches more than 40% prior to the stationary phase, thereby reducing the expression effect.

CONTENT OF THE PRESENT INVENTION

The technical problem to be solved by the present invention is that the current screening methods of constitutive promoters are complicated, and the expression plasmid constructed by the screened promoter is easily lost in the growth of the host, and also has adverse effects on the growth and metabolism of the host. How to establish a rapid screening method for constitutive promoters to screen endogenous promoter with high viability in the stationary phase, and how to ensure the stability of plasmid constructs containing the promoters in the stationary phase of bacteria growth is the problem needed to be solved.

The object of the present invention is to establish a method for finding a promoter gene and using it to construct a constitutive high-efficiency expression plasmid, wherein the promoter gene is silent in the logarithmic phase of bacteria growth and efficiently expressed in the stationary phase of bacterial growth. In the present invention, we used analytic data of transcriptome sequencing to find a class of promoters which can regulate the low expression of a gene of interest in the logarithmic phase and high expression in the stationary phase. Generally, such promoters are all regulatable promoters. We intercepted a variety of gene fragments from these promoters and constructed a series of *Corynebacterium* constitutive expression vectors. The series of expression vectors used green fluorescent protein (EGFP) as a marker gene to detect the activity of each promoter fragment and evaluate the passage stability of each probe plasmid, thereby screening a series of promoters with low activity in the logarithmic phase and high activity in the stationary phase, evaluating the passage stability of plasmids containing each promoter, and further screening promoters for stabilizing plasmids.

The technical solutions adopted in this aspect are:

A method for screening a *Corynebacterium* constitutive expression vector promoter on the basis of transcriptome sequencing, comprising:

analyzing the transcription level of each gene of the *Corynebacterium* in logarithmic phase and stationary phase, and screening a class of genes with low transcription levels in the logarithmic phase and high transcription levels in the stationary phase are screened by analyzing the transcription abundance of each gene in two phases;

analyzing the promoter regions of genes using promoter prediction software, amplifying the promoter fragments of genes by PCR and incorporating the DNA fragment of the promoter and marker gene into an expression vector to construct a promoter probe vector;

electroporating the probe vector into host cells, and culturing the host cell to the logarithmic phase and the stationary phase, then detecting the OD value of the growth bacteria and fluorescent protein expression using multifunctional microplate reader, while carrying out continuous passage under an antibiotic-stress free condition;

selecting host cells having low fluorescence value in the logarithmic phase and high fluorescence value in the stationary phase of the probe vector, and the promoter contained in the host cells that has been continuously passaged for 50 generations without plasmid lost is the *Corynebacterium* constitutive expression vector promoter.

A *Corynebacterium* constitutive expression vector promoter screened by the abovesaid method, wherein the nucleotide sequence of the promoter is set forth in SEQ ID NO: 1, SEQ ID NO: 2 or SEQ ID NO: 3.

A *Corynebacterium* constitutive expression vector comprising the abovesaid *Corynebacterium* constitutive expression vector promoter.

The abovesaid *Corynebacterium* constitutive expression vector, wherein it is constructed by inserting a gene of interest and the abovesaid *Corynebacterium* constitutive expression vector promoter at the restriction site of the plasmid HY-P19, wherein the nucleotide sequence of the plasmid HY-P19 is shown in SEQ ID NO: 4, and the nucleotide sequence of the gene of interest is set forth in SEQ ID NO: 5, SEQ ID NO: 6 or SEQ ID NO: 7. Among them, the nucleotide sequence of the gene of interest is set forth in SEQ ID NO: 5, provided that the nucleotide sequence of the *Corynebacterium* constitutive expression vector promoter is set forth in SEQ ID NO: 1; the nucleotide sequence of the gene of interest is set forth in SEQ ID NO: 6, provided that the nucleotide sequence of the *Corynebacterium* constitutive expression vector promoter is set forth in SEQ ID NO: 2; the nucleotide sequence of the gene of interest is set forth in SEQ ID NO: 7, provided that the nucleotide sequence of the *Corynebacterium* constitutive expression vector promoter is set forth SEQ ID NO: 3.

The recombinant strain obtained by electroporating the host cell *C. glutamicum* with the expression vector, preferably the accession number of the host cells *C. glutamicum* is CCTCC NO: M2016609, the strain has been deposited at the China Center for Type Culture Collection on Nov. 1, 2016.

Use of the recombinant strain in the production of isoleucine.

The beneficial effect of the present invention is that the expression vector constructed by such promoter has a low expression level of the target protein in the logarithmic phase, but the expression level of the target protein in the stationary phase is greatly increased compared to the logarithmic phase, and the adverse effect on the growth of the host bacteria is low and the stability of plasmid passage is high. The promoter is suitable for vector construction of the gene of interest which does not need expression in the logarithmic phase but needs high expression in the stationary phase. It is especially suitable for the construction of engineering strains for amino acid fermentation.

The promoter, expression vector and recombinant strain screened herein, which can increase acid yield and conversion rate of glucose to acid (conversion rate=total weight of target amino acid produced in fermentation broth/weight of glucose used for fermentation)×100%), and reduce the heteroacid yield when isoleucine is produced by fermentation, has a high application prospect.

DEPOSIT INFORMATION OF BIOLOGICAL MATERIAL

The *Corynebacterium glutamicum* strain H5 of the present invention was deposited at the China Center for Type Culture Collection (CCTCC) on Nov. 1, 2016, and confirmed viable on Nov. 12, 2016. The deposit address is: Wuhan University, Wuhan, China, Zip Code:430072, the accession number is: CCTCC NO: M2016609, the culture name is *Corynebacterium glutamicum* H5, and the classification is *Corynebacterium glutamicum*.

DETAILED DESCRIPTION OF THE PREFERRED EMBODIMENT

Figure 1:
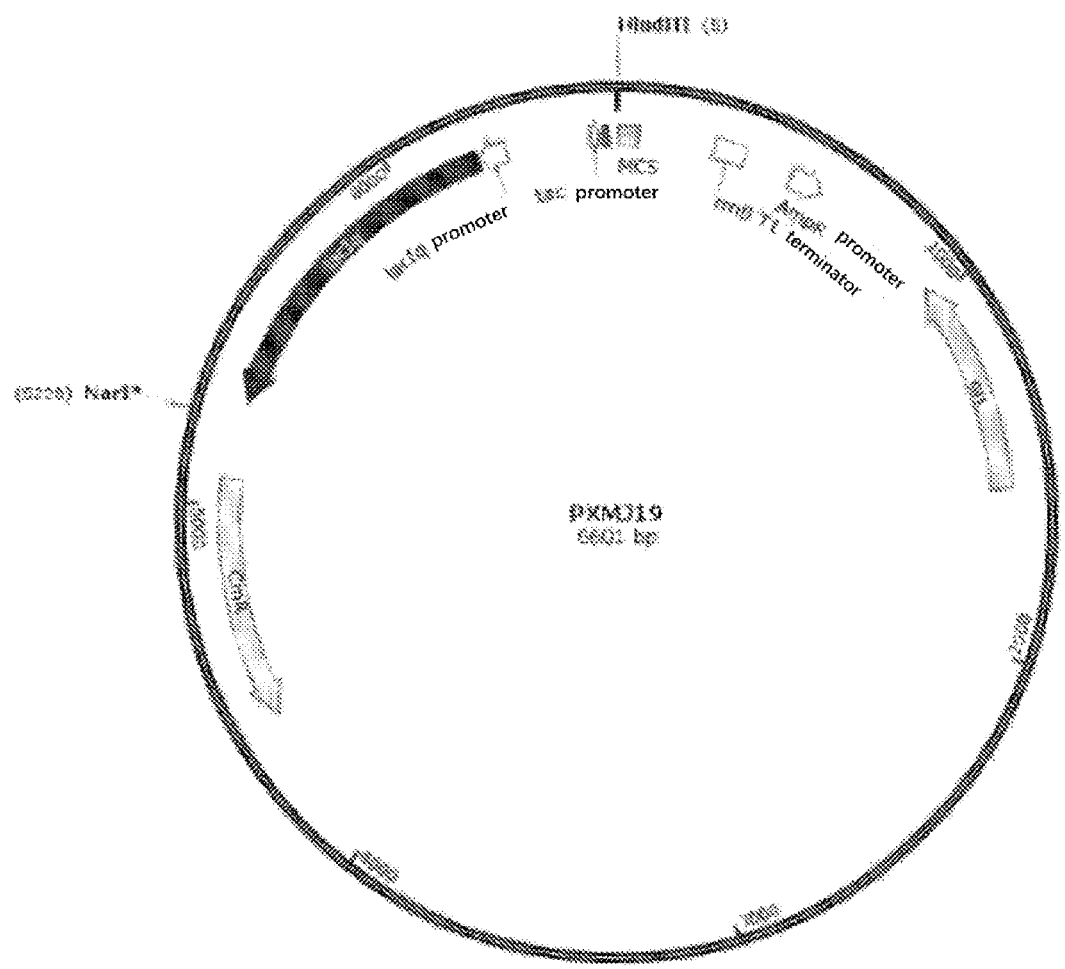
FIG. 1 shows the original plasmid PXMJ19.

The present invention will now be illustrated in detail by way of embodiments.

Embodiment 1

1. Preparation of Transcriptome Sequencing Sample and Analysis of Transcription Information:

Bacterial culture: The L-isoleucine-producing *Corynebacterium glutamicum* without plasmid (*Corynebacterium glutamicum* H5 strain, deposited at the China Center for Type Culture Collection on Nov. 1, 2016, and the accession number of which is CCTCC NO: M2016609) was picked and inoculated to LB medium, and cultured overnight at 31° C. The obtained bacterial liquid was centrifuged and resuspended in an equal volume of sterile water, then inoculated to LBG fresh sterile medium at a percentage of 5%, and cultured at 31° C. and 200 rpm until the mid-log phase and the early stationary phase. The fermentation broth was taken out, and mixed immediately with an equal volume of RNA Protect® Bacteria Reagent (QIAGEN). After centrifugation at 5000 rpm for 10 min, 100 mg of wet bacteria were weighed and quickly stored in liquid nitrogen.

RNA extraction: The sample stored in liquid nitrogen was placed in a mortar precooled with liquid nitrogen, and an appropriate amount of liquid nitrogen was added to ensure that the mortar always contains a certain amount of liquid nitrogen. The sample was ground into powder, and then RNA of which was extracted according to the experimental procedure provided by QIAGEN RNeasy Plant Mini Kit. The extracted sample was tested by 1% agarose gel, which requires that the sample cannot be contaminated with protein, i.e. there was no obvious bright bands in the pores of agarose gel. The concentration of nucleic acid was measured by NanoDrop Spectrophotometer. The concentration of the sample in mid-log phase was 421 ng/µl, and that in stationary phase was 237 ng/µl, and the requirements of no obvious protein contamination and nucleic acid concentration reaching >60 ng/µl were met.

2. Transcriptome sequencing: extracted RNA samples were sequenced by Beijing Novogene Corporation. The sequencing process was as follows: After the sample was qualified, rRNA was removed by Ribo-zero kit to enrich the mRNA. Subsequently, the fragmentation buffer was added to break the mRNA into short fragments. mRNA was used as a template to synthesize a single stranded cDNA with random hexamers. Then, buffer, dNTPs (dTTP in dNTP was replaced with dUTP), DNA polymerase I and RNase H polymerase were added to synthesize the double-stranded cDNA. Then, the double-stranded cDNA was purified with AMPure XP beads, and the second strand of the cDNA containing U was degraded with USER enzyme. The purified double-stranded cDNA was firstly end-repaired, A-tailed and ligated to sequencing adaptor, and then the fragment size was selected using AMPure XP beads. Finally, PCR amplification was performed and the PCR products were purified with AMPure XP beads to obtain a final library. After the library was constructed, preliminary quantification was performed using Qubit 2.0, and the library was diluted to 1 ng/μl. Then, the insert size of the library was detected using Agilent 2100. After the insert size met the expectation, the effective concentration of the library was accurately quantified (effective library concentration >2 nM) by using Q-PCR method to ensure the quality of the library. Once the library was qualified, different libraries were pooled according to the requirement of the effective concentration and target raw data volume, and HiSeq/MiSeq sequencing was performed.

3. Bioinformatics analysis process: The sequencing results were analysed by Beijing Novogene Corporation. After the original Sequenced Reads were obtained, bioinformatics analysis was performed by using reference sequence or reference genome of the relevant species. The main processes of bioinformatics analysis were as follows:

Original sequence data→Quality assessment of sequencing data→Alignment analysis with reference sequence→Gene expression level analysis→Overall quality assessment of RNA-seq→Gene differential expression analysis→GO enrichment analysis of differential gene or KEGG enrichment analysis of differential gene.

The bioinformatics reference species of the sample of the present invention is *Corynebacterium glutamicum* ATCC 13032 (purchased from Shanghai Fuxiang Biotechnology Co., Ltd.), and the reference genome is linked to ncbi as https://www.ncbi.nlm.nih.gov/Nuccore/NC_006958.1.

According to the table of the information analysis data finally provided, the expression abundance of each gene in the logarithmic phase and the stationary phase was analyzed, and 10 genes and transcription analysis information in Table 1 were screened. The consistent characteristics of the 10 genes were: the transcription level was low in the logarithmic phase, while the transcription level was high in the stationary phase. By prediction of the operon, the genes CGTRNA_RS10085 and CGTRNA_RS10080 belong to the same operon, CGTRNA_RS07920, CGTRNA_RS07925, CGTRNA_RS07930 belong to the same operon, CGTRNA_RS00965, CGTRNA_RS00970 belong to the same operon, and the same operon shares one promoter.

TABLE 1

The *Corynebacterium* glutamate transcriptome analysis of gene with high transcript abundance in S phase and low transcript abundance in L phase

| Gene Name | Strand | start | end | length | S1_fpkm | L1_fpkm |
|---|---|---|---|---|---|---|
| CGTRNA_RS10085 | − | 2142201 | 2143517 | 1317 | 27347.52 | 148.9929 |
| CGTRNA_RS10080 | − | 2141798 | 2142136 | 339 | 24497.2 | 543.2887 |
| CGTRNA_RS10840 | + | 2320501 | 2321934 | 1434 | 13058.69 | 838.0642 |
| CGTRNA_RS07910 | − | 1672737 | 1673144 | 408 | 7453.836 | 37.12523 |
| CGTRNA_RS07920 | − | 1674757 | 1675572 | 816 | 3383.739 | 15.18759 |
| CGTRNA_RS07925 | − | 1675587 | 1676735 | 1149 | 2442.069 | 7.789865 |
| CGTRNA_RS07930 | − | 1676732 | 1678090 | 1359 | 5493.98 | 22.03821 |
| CGTRNA_RS00965 | + | 195241 | 199773 | 4533 | 6137.992 | 54.29964 |
| CGTRNA_RS00970 | + | 199773 | 201293 | 1521 | 4023.859 | 33.94991 |
| CGTRNA_RS04670 | + | 988209 | 989480 | 1272 | 2037.631 | 8.931068 |

4. Promoter region screening: by means of NCBI blast, the predicted gene fragments were aligned with the genome of the *C. glutamicum* sequenced in the laboratory to find the corresponding gene sequence. The promoter region of each gene was predicted by searching literature or applying promoter prediction software, and 2-3 fragments from the promoter region of each gene were selected according to the predicted functional region for promoter activity detection.

(1) promoter region fragments of gene CGTRNA_RS10085:
RS10085seq1:
CTATTGAAATTAGTTTCTGTAGGTCTATAGTTAGAGCTGGTTCAAGGGGT

GTCAATCCCAAAAGGCACTCCTTGAACTCATGAAAAAGCTTGACAAAACT

TCAACGTCAAAGGAGGTCATCCACGCT

RS10085seq2:
CTATTCTATAGATCTATTGAAATTAGTTTCTGTAGGTCTATAGTTAGAGC

TGGTTCAAGGGGTGTCAATCCCAAAAGGCACTCCTTGAACTCATGAAAAA

GCTTGACAAAACTTCAACGTCAAAGGAGGTCATCCACGCT

RS10085seq3:
ACTTAACAATTCATTAAATTACCTGTTAAACTATAGAAAATATCCAAAAC

CCTCCAAAACCTATTCTATAGATCTATTGAAATTAGTTTCTGTAGGTCTA

TAGTTAGAGCTGGTTCAAGGGGTGTCAATCCCAAAAGGCACTCCTTGAAC

TCATGAAAAAGCTTGACAAAACTTCAACGTCAAAGGAGGTCATCCACGCT (2) promoter region fragments of gene CGTRNA_RS10840
RS10840 seq1:
TCAAAGGTCAGCAATTGTGAACAAAGCTACAAATAAACCGTTCCACCCAT

GTCAATGAGGAGTCACC

RS10840 seq2:
GCAGTCAAAAGGCGTTGCTTTTCGACGTCGCAAAGCGCAATTTCCTACCT

TTAAGATCCTAATCTGTTGAGGTCAGCCACAATTTTTCAGAAAAGTTTTG

-continued
ATAGATCGACAGGTAATGCTTTATACTGACAACGTCGCAAGGACTACATT

TGCAGCCAAGTCTACTACTTGATCTTCAAAGGTCAGCAATTGTGAACAAA

GCTACAAATAAACCGTTCCACCCATGTCAATGAGGAGTCACC (3) promoter region fragments of gene
CGTRNA_RS07910
RS07910 seq1:
ACTTGGTTCCTGCCCAACAACCCAGTGGACTTCCAGCCGGAAAATCTGCC

ATGCTTCATCCGTGACCGTG

RS07910 seq2:
GCGATCACGTAGTCATCCAAGCAGGCGAAGAAACCACAATCGTGGACCGC

GTTATCGTCACCACCGGCAGCTGGACAAGCGAGCTCGTGCCCTCCATCGC

GCCACTGCTTGAAGTGCGACGCCTAGTGCTCACTTGGTTCCTGCCCAACA

ACCCAGTGGACTTCCAGCCGGAAAATCTGCCATGCTTCATCCGTGACCGT

G (4) promoter region fragments of gene
CGTRNA_RS07930
RS07930 seq1:
CGGAATAGAAAATACTCCGCTCGACAGCATCACTTAGCTGAAAGGCCTTT

AAC

RS07930 seq2:
GAAACTGGACTAGGTTTATCTATAGCGGAATAGAAAATACTCCGCTCGAC

AGCATCACTTAGCTGAAAGGCCTTTAAC

RS07930 seq3:
GCAGGTTAAAACGCTGCCATAGGGGATTTTTCGGCTGGGGAGACGTGGTG

TAAGTGCGGGTTAAAAACGTGACCTTCGTTATAAAAACAGAAATCTATAG

AACGATAGGTAGAAACTGGACTAGGTTTATCTATAGCGGAATAGAAAATA

CTCCGCTCGACAGCATCACTTAGCTGAAAGGCCTTTAAC (5) promoter region fragments of gene
CGTRNA_RS00965
RS00965 seq1:
CTTGCGTTGCAGGTAGTGCGCCTGATTTTCTTATTATCGAACGATTGATA

GAAACAGGATTAAAGTGAGGTATCCCGC

RS00965 seq2:
TTTTATCTTCTTTCACGGGGTGGATAGGCGAACATCTTCTACCATATCCT

GTGATGTGTAACACAGGAGCGTAATCTGACCTCCCGTTTTCCTATAGATT

GATCGAAAGTAACCCTTTTGTTACTTGCGTTGCAGGTAGTGCGCCTGATT

TTCTTATTATCGAACGATTGATAGAAACAGGATTAAAGTGAGGTATCCCG

C (6) promoter region fragments of gene
CGTRNA_RS04670
RS04670 seq1:
AGGCTGACAGAAACTCTAAAAACTATAGAGCTATAGAAACCTTAACTTCG

GAGGTATCC

RS04670 seq2:
GTGGGCGCTGGGCCATAGTCGCCCCAGCTCAGCGAAGTTGTACGCCGGCG

TTGCCTGCTTGTCGACGTTTTTTGCCACTTCCCTTAATTCGGGGGTGGCT

GAAATGTAAGACACGTCACTACATTTAAGCTCAAAAACAACTACCTATAG

GCTGACAGAAACTCTAAAAACTATAGAGCTATAGAAACCTTAACTTCGGA

GGTATCC

5. Construction of Promoter Probe Vector and Detection of Fluorescence:

(1) Primer synthesis: The primers were designed by snapgene software, and synthesized by Wuhan TianyiHuiyuan Corporation. The sequences of synthetic primer are shown in Table 2 below.

TABLE 2 primer sequences for the construction of the probe vector

| Primer Name | Primer Sequence |
|---|---|
| RS10085SEQ1FP | TGCCTGCAGGTCGACTCTAGACTATTGAAATTAGTTTCTG |
| RS10085SEQ2FP | TGCCTGCAGGTCGACTCTAGACTATTCTATAGATCTATTG |
| RS10085SEQ3FP | TGCCTGCAGGTCGACTCTAGAACTTAACAATTCATTAAAT-TACC |
| RS10085SEQ1RP | CTCGCCCTTGCTCACCATAGCGTGGATGACCTCCTTTG |
| RS10840SEQ1FP | TGCCTGCAGGTCGACTCTAGATCAAAGGTCAGCAATTG |
| RS10840SEQ2FP | TGCCTGCAGGTCGACTCTAGAGCAGTCAAAAGGCGTTGC |
| RS10840SEQ1RP | CTCGCCCTTGCTCACCATGGTGACTCCTCATTGACATG |
| RS07910SEQ1FP | TGCCTGCAGGTCGACTCTAGAACTTGGTTCCTGCCCAAC |
| RS07910SEQ2FP | TGCCTGCAGGTCGACTCTAGAGCGATCACGTAGTCATCC |
| RS07910SEQ1RP | CTCGCCCTTGCTCACCATCACGGTCACGGATGAAGC |
| RS07930SEQ1FP | TGCCTGCAGGTCGACTCTAGACGGAATAGAAAATACTCC |
| RS07930SEQ2FP | TGCCTGCAGGTCGACTCTAGAGAAACTGGACTAGGTT |
| RS07930SEQ3FP | TGCCTGCAGGTCGACTCTAGAGCAGGTTAAAACGCTGC |
| RS07930SEQ1RP | CTCGCCCTTGCTCACCATGTTAAAGGCCTTTCAGCTAA |

TABLE 2-continued primer sequences for the construction of the probe vector

| Primer Name | Primer Sequence |
|---|---|
| RS00965SEQ1FP | TGCCTGCAGGTCGACTCTAGACTTGCGTTGCAGGTAG |
| RS00965SEQ2FP | TGCCTGCAGGTCGACTCTAGATTTTATCTTCTTTCACGGGGTG |
| RS00965SEQ1RP | CTCGCCCTTGCTCACCATGCGGGATACCTCACTTTAATC |
| RS04670SEQ1FP | TGCCTGCAGGTCGACTCTAGAAGGCTGACAGAAACTC |
| RS04670SEQ2FP | TGCCTGCAGGTCGACTCTAGAGTGGGCGCTGGGCCA |
| RS04670SEQ1RP | CTCGCCCTTGCTCACCATGGATACCTCCGAAGTTAAG |
| EGFP-FP | ATGGTGAGCAAGGGCGAGGA |
| EGFP-RP | CAAAACAGCCAAGCTGAATTCTTACTTGTACAGCTCGTCCATGCC |

(2) Genomic extraction: *Corynebacterium glutamicum* H5 was picked and inoculated to LB medium, and incubated at 31° C. overnight. Removing the supernatant by centrifugation, the bacterial genome was extracted according to the protocol of the Tiangen Genome Extraction Kit. The concentration of the nucleic acid from the extracted genome was detected using a NanoDrop Spectrophotometer, and the concentration of the nucleic acid for PCR amplification was controlled between 100 and 200 ng/μl.

(3) PCR amplification: each synthetic primer was diluted with water to a final concentration of 10 μM, and the amplification was carried out using TransStart FastPfu Fly DNA Polymerase. The PCR system contained 1 μl of genomic template, 1 μl of forward primer (10 μM), 1 μl of reverse primer (10 μM), 10 μl of 5*TransStart FastPfu FlyBuffer, 4 μl of 2.5 mM Dntps, 1 μl of TransStart FastPfu Fly DNA Polymerase, and ddH$_2$O 32μl. The PCR amplification process was 95° C. for 2 min, 32 cycles of 95° C. for 20 s, 55° C. for 20 s and 72° C. for 10 s–1 min, and 72° C. for 5 min. The amplified DNA fragments with recombinant adaptors RS10085seq1, RS10085seq2, RS10085seq3, RS10840seq1, RS10840seq2, RS07910seq1, RS07910seq2, RS07930seq1, RS07930seq2, RS07930seq3, RS00965seq1, RS00965seq2, RS04670seq1, RS04670seq2, and EGFP were then obtained.

(4) Plasmid digestion and DNA synthesis: the original plasmid PXMJ19 was double digested with NEB restriction endonuclease NarI and HindIII, the original lacIq and promoter Ptac were removed in a 50 μl of enzyme digestion system containing 5-10 μl of plasmid, 1 μl of NarI, 1 μl of HindIII, 5 μl of cutsmart, and 33-38 μl of ddH$_2$O.

DNA sequence hy-dna1 shown below was synthesized by Wuhan Tianyi Huiyuan:

gcatccggggctgatccccggcgcctaactaactaactcgagcttaagag gcctaagcttgcatgcctgcaggtcgact (5) DNA recovered by agarose electrophoresis: The PCR products and the digested products were aliquoted with 10*loading buffer and 50 μl of which were loaded onto a 1.5% agarose gel, takara 2000 DL DNA marker was used as a control, and electrophoresis was carried out at 70 V for 40 min. According to the instruction of marker bands, PCR amplified bands were recovered using takara DNA recovery kit. The DNA fragments with recombinant adaptor RS10085seq1 (167 bp), RS10085seq2 (180 bp), RS10085seq3 (240 bp), RS10840seq1 (107 bp), RS10840seq2 (282 bp), and RS07910seq1 (110 bp), RS07910seq2 (241 bp), RS07930seq1 (93 bp), RS07930seq2 (118 bp), RS07930seq3 (229 bp), RS00965seq1 (118 bp), RS00965seq2 (241 bp), RS04670seq1 (99 bp), RS04670seq2 (247 bp), EGFP (760 bp) were then obtained.

(6) In vitro recombination: The digested products were in vitro recombined with the synthetic DNA fragment hydna1 using Vazyme one Step Cloning Kit, and the recombinant products were directly transformed into *E. coli*.

(7) Preparation of *E. coli* competent cells: *E. coli* competent cells DH5a were prepared using Beyotime Supercompetent Cell Preparation Kit, and the prepared competent cells were stored in a refrigerator at −80° C. until use.

(8) Transformation: The DH5a competent cells were slowly thawed on ice, and the in vitro recombinant products were pipetted into the competent cell. The centrifuge tube was gently flicked with finger to mix the bacteria and the recombinant products, and placed in an ice bath or ice water bath for 30 minutes. Then the centrifuge tube was placed in a water bath at 42° C., and heated shock for 2 minutes Immediately after heat shock, the centrifuge tube was placed in an ice water bath for 2 minutes. 900 ml of LB was aliquoted and incubated at 37° C. and 200 rpm for 1 hour. The supernatant was removed after centrifugation, and the obtained cells were spread on LB solid plate containing 25 μg/ml chloramphenicol, and cultured overnight at 37° C.

(9) Transformants verification and plasmid extraction: transformants grown on the resistant plates after transformation were sent to Wuhan Tianyi Huiyuan for sequencing analysis, and the transformants with correct sequence were transferred into a tube with 5 ml LB containing a final concentration of 25 μg/mol of chloramphenicol. The tube was cultured at 37° C. and 200 rpm overnight, and plasmid was extracted using Takara plasmid kit to make the concentration of which between 200-400 ng/μl. The constructed plasmid was named HY-P19, the sequence of which is shown in SEQ ID NO: 4.

HY-P19 was digested with NEB restriction enzyme XbaI and EcoRI in a 37° C. water bath for 1 h, and the amount of the plasmid was 1 μg in a 50 μl of digestion system. The digestion system includes 5-10 μl of plasmid, 1 μl of XbaI, 1 μl of EcoRI, 5 μl of cutsmart, and 33-38 μl of ddH$_2$O. The digested products of HY-P19 were recovered, and recombined in vitro with each promoter fragment and EGFP fragment using Vazyme one Step Cloning Kit. The other experimental processes were the same as (7)-(9) mentioned-above.

```
DNA seq of green fluorescent protein EGFP
fragment: 720 bp
ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTA

CGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAGTAA
```

Figure 2:
FIG. 2 shows the synthetic DNA fragment hy-dna1.
Figure 3:
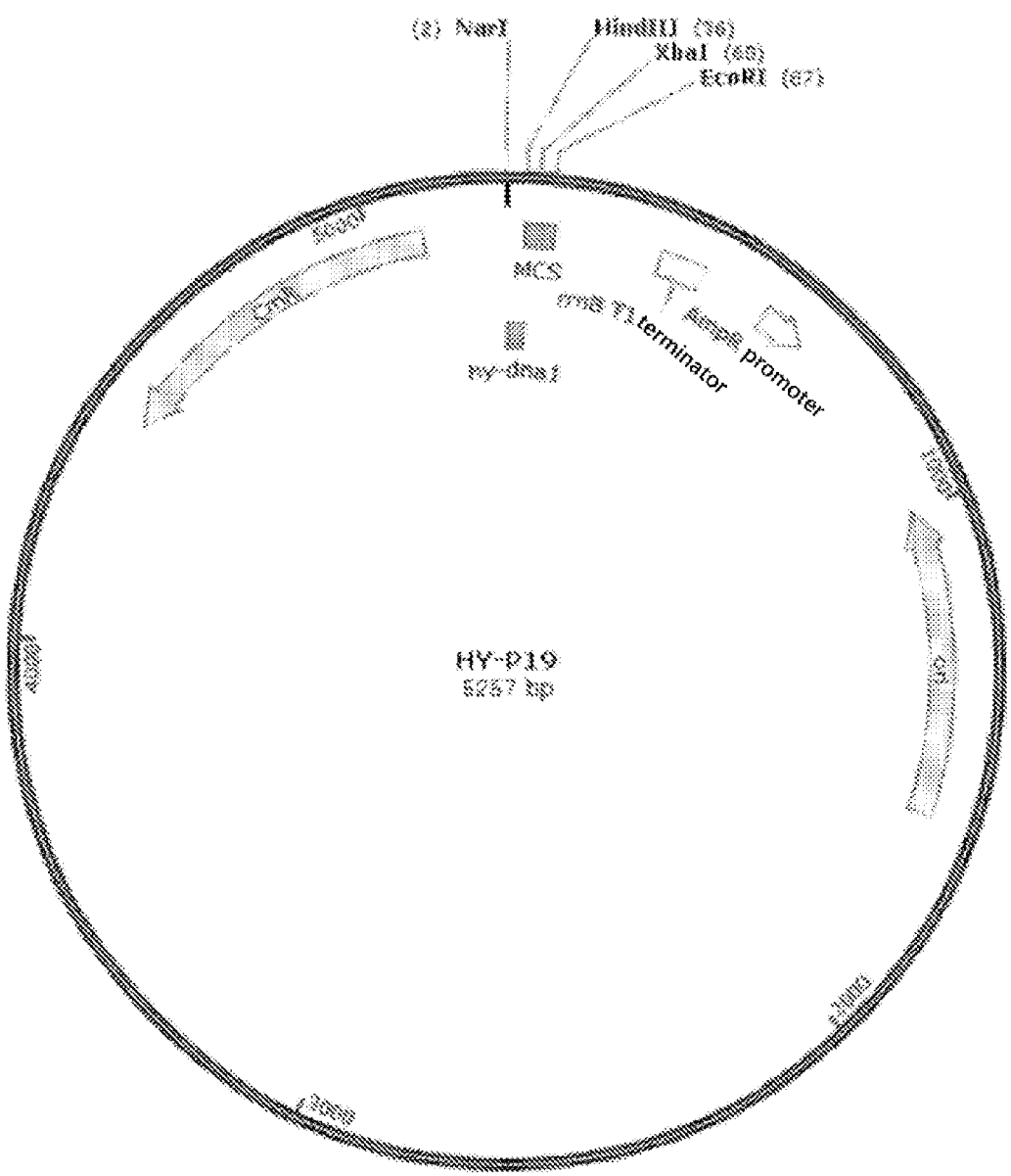
FIG. 3 shows plasmid HY-19 constructed after in vitro recombination.
Figure 4:
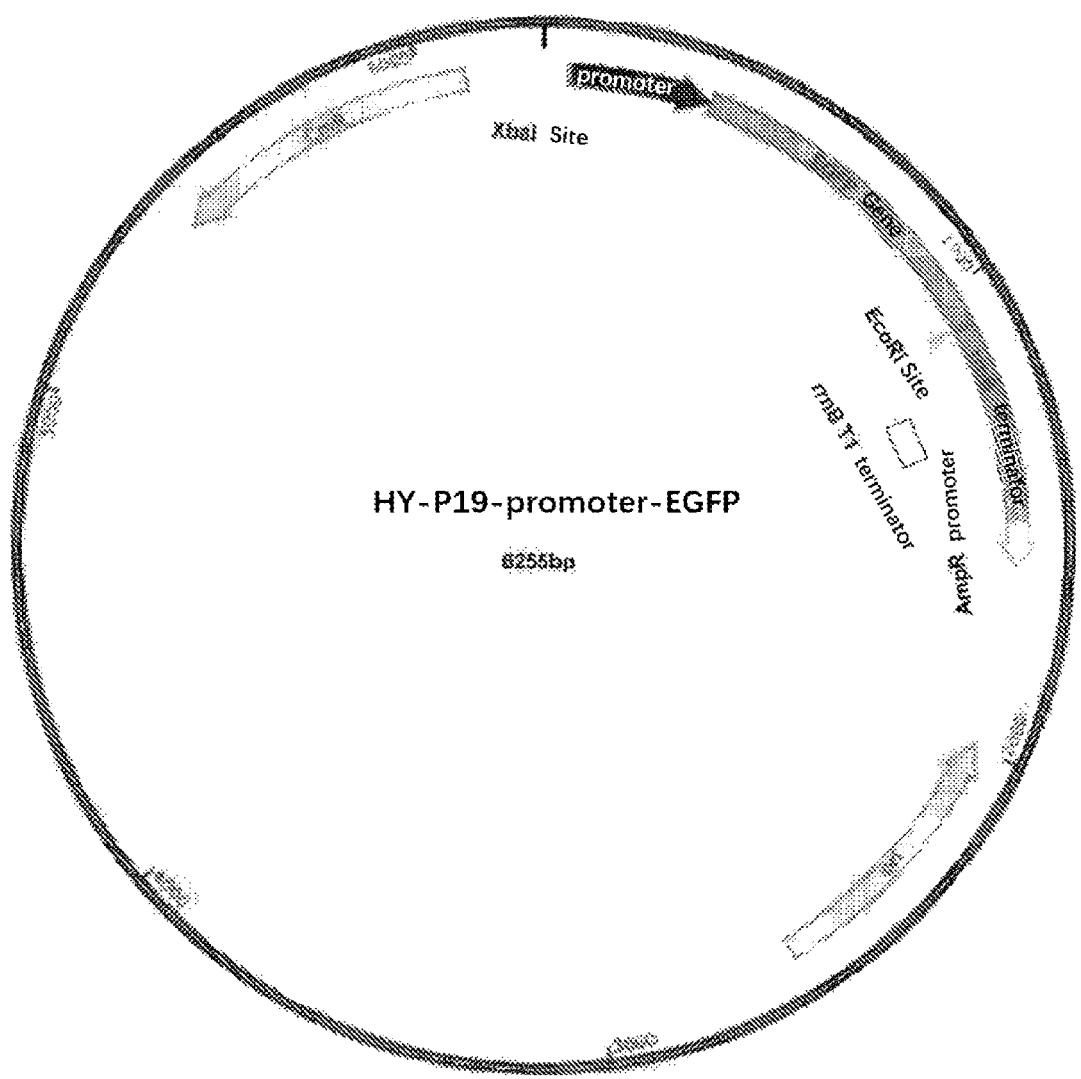
FIG. 4 shows the recombinant plasmid HY-P19-promoter-EGFP.

A series of plasmids HY-P19-promoter-EGFP containing probe vectors with different promoters were constructed, and the construction process is as follows: the original plasmid PXMJ19 shown in FIG. 1 was digested with NarI and HindIII, and digested products were recovered after digestion. The digested product and the synthesized DNA fragment shown in FIG. 2 were recombined in vitro by one-step cloning. After the recombinants were transformed into DH5a, positive clones were picked and verified by sequencing, then the verified plasmid was extracted to obtain plasmid HY-P19 of FIG. 3. HY-P19 was digested with XbaI and EcoRI, and digested products were recovered. The digested products were further recombined in vitro with a series of synthesized promoter fragments and PCR-amplified EGFP fragment. After the recombinants were transformed into DH5α, positive clones were picked and verified by sequencing. Thereafter, the plasmid was extracted to obtain a probe vector with a series of promoters and the marker gene EGFP shown in FIG. 4. The probe vectors containing the promoter fragments were named PRS10085seq1, PRS10085seq2, PRS10085seq3, PRS10840seq1, PRS10840seq2, PRS07910seq1, PRS07910seq2, PRS07930seq1, PRS07930seq2, PRS07930seq3, PRS00965seq1, PRS00965seq2, PRS04670seq1, PRS04670seq2, respectively.

(10) Preparation of Electroporation Competent *C. glutamicum* Cells:

① A single colony was picked from the fresh LB plate (cultured for about 12 h), and inoculated into a test tube containing 5 mL of LBG liquid, and cultured at 30° C., 220 rpm overnight.

② 2 mL of bacterial culture from step ① was transferred into a 1 L conical flask containing 100 mL of EPO (comprising 5 g/L of yeast powder, 10 g/L of peptone, 10 g/L of Nacl, 25 g/L of glycine, and 1 g/L of Tween), and incubated at 30° C. until the OD value of which reached between 1.0 and 1.5 (approximately 4-5 h).

③ All the culture was transferred into a 50 mL centrifuge tube pre-cooled at 4° C. under sterile conditions, then the tube was placed on ice for 2 minutes.

④ After Centrifuging at 7000 rpm for 20 minutes at 4° C. and removing the supernatant, the centrifuge tube was inverted on a sterile filter paper to absorb the residual Epo medium.

⑤ The bacteria pellets were resuspended in 40 mL of 10% glycerol solution pre-cooled at 4° C. and shaken gently, centrifuged at 7000 rpm for 10 minutes. The supernatant was then removed.

⑥ Step 5 was repeated twice.

⑦ 1 mL of pre-cooled 10% glycerol solution was pipetted into the centrifuge tube and the bacteria pellet was resuspended by gently blowing.

⑧ Finally, the competent cells were aliquoted into 1.5 mL sterile EP tubes with 0.1 mL per tube. Stored in an ultra-low temperature freezer at −80° C.

(11) Electro-Transformation of *Corynebacterium glutamicum*:

① One tube of *C. glutamicum* competent cells stored at −80° C. was taken out and placed on ice until thawed.

② The sample plasmid DNA was pipetted into the thawed competent cells and the EP tube was flicked with fingers to ensure that the DNA and competent cells were well mixed.

③ The competent cells containing DNA plasmid was pipetted into a pre-cooled electroporation cuvette (with a pore size of 2 mm) and the cuvette was quickly dried with absorbent paper.

④ The electroporation cuvette was placed into the electroporator, and electroporated under 1800V for 5 milliseconds.

⑤ The cell solution was quickly pipetted into an EP tube containing 5 mL of LBHIS pre-warmed at 46° C., and heat shock was carried out for exactly 6 minutes.

⑥ The EP tube was cultured by shaking at 30° C. and 200 rpm, and the cells were resuscitated for 60 minutes.

⑦ After centrifugation at 7,000 rpm for 2 minutes at room temperature and removing most of the supernatant, the cells were resuspended in the remaining medium and spread with a glass rod on LBCIS solid medium supplemented with 10 μg/mL of chloramphenicol.

⑧ After standing at room temperature for about 1 hour, the liquid on the surface of the solid medium was fully absorbed, then the plate was inverted and cultured in a constant temperature incubator at 30° C. for 36 hours, and the grown transformants were the strain containing various probe vector.

(12) Fluorescence Detection of *Corynebacterium glutamicum* Transformants

The *Corynebacterium glutamicum* transformants containing different promoter fragments were transferred into a tube with 5 ml LBG medium and cultured at 30° C. to an OD600 of 2.0 (logarithmic phase) and 3.2 (stationary phase), respectively. After supernatant was removed by centrifugation, the cells were washed twice with PBS solution, and resuspended in the same volume of PBS. 200 μl of the resuspended cells were aliquoted into a 96-well plate with black bottom and fluorescence value was detected using a multi-plate reader TECANM1000. The detected fluorescence values of the probe plasmids in the logarithmic phase and the stationary phase of the host bacteria are shown in Table 3. From the table we can see that when a same gene promoter has different promoter fragments, the data of different promoter activity can be obtained by the detection of fluorescence value, which is related to the regulation of promoter region of the gene. Promoter fragments with a low fluorescence value in the logarithmic phase and a high fluorescence value in the stationary phase are the ones we need. Promoter fragments RS10085seq2, RS10085seq3, RS10840seq2, RS07910seq2, RS07930seq3, RS00965seq2, RS04670seq2 showed our desired screening characteristics during the expression of the probe vector.

TABLE 3

Statistics of fluorescence detection and plasmid passage of each probe plasmid in two phases of host bacteria

| Each probe vector | Fluorescence value in logarithmic phase | Fluorescence value in stationary phase | Number of stable passages of each plasmid |
|---|---|---|---|
| Control, plasmid-free | 2871 | 8024 | — |
| PRS10085seq1 | 150352 | 231073 | 8 |
| PRS10085seq2 | 6364 | 241445 | 50 |
| PRS10085seq3 | 6191 | 225450 | 50 |
| PRS10840seq1 | 102254 | 184533 | 6 |
| PRS10840seq2 | 11022 | 177132 | 50 |
| PRS07910seq1 | 9551 | 102310 | 6 |
| PRS07910seq2 | 3564 | 98756 | 50 |
| PRS07930seq1 | 12029 | 146021 | 5 |
| PRS07930seq2 | 8211 | 133602 | 8 |
| PRS07930seq3 | 3321 | 122564 | 50 |
| PRS00965seq1 | 11083 | 85472 | 11 |
| PRS00965seq2 | 5412 | 77450 | 50 |
| PRS04670seq1 | 5441 | 35390 | 14 |
| PRS04670seq2 | 3698 | 28428 | 50 |

Note:
stable passages means that more than 90% of the bacteria contain plasmids, passaging for 50 times means after 50 passages, more than 90% of the bacteria still contain plasmid.

6. Plasmid Passage Stability of Each Promoter Probe Vector

The recombinant bacteria containing each promoter probe vector were inoculated into LBG medium and the inoculation amount for passaging was 5%. Without antibiotics pressure, the recombinant bacteria were cultured on a rotary shaker at 30° C. and 190 rpm for 24 h, i.e. one generation of passaging was done. Continuous passaging was carried out, each passage of bacteria was diluted and spread on the plates, and the bacteria with same diluted concentration were spread on chloramphenicol-containing plates and chloramphenicol-free plates. The loss rate of the plasmid=(the number of colonies grown on the chloramphenicol-containing plates−the number of colonies grown on the chloramphenicol-free plates)/the number of colonies grown on the chloramphenicol-containing plates×100%. It is considered that the passaging of plasmids is stable while the loss rate of the plasmid is less than or equal to 10%, and it is considered that the passaging of plasmids is unstable when the loss rate of the plasmid is more than 10%. The number of stable passages of bacteria containing each probe plasmid is shown in Table 3.

From Table 3, we can conclude that when passaged to the 50th generation, loss rate of the plasmids PRS10085seq2, PRS10085seq3, PRS10840seq2, PRS07910seq2, PRS07930seq3, PRS00965seq2, and PRS04670seq2 was less than or equal to 10%, showing a good stability.

Embodiment 2 Expression Vector Constructed Using Promoter Fragment RS10085seq2 and Application Thereof 1. Construction of Expression Vector HY-P19-RS10085seq2-ilvA The key gene for isoleucine metabolism of *Corynebacterium glutamicum* is threonine dehydratase, and the gene was name ilvA (the sequence of which is shown in SEQ ID NO: 5). Using the screened promoter fragment RS10085seq2 as a promoter and ilvA as a target gene, the expression vector HY-P19-RS10085seq2-ilvA was constructed.

DNA fragment amplification: plasmid PRS10085seq2 was used as a template, and the upstream and downstream primers were as follows:

```
RS10085seq2Fp:
tgcctgcaggtcgactctagaCTATTCTATAGATCTATTG

RS10085seq2Rp:
AGCGTGGATGACCTCCTTTGA
```

The DNA fragment RS10085seq2 was amplified using TransStart FastPfu Fly DNA Polymerase. The PCR system comprised: 1 μl of PRS10085seq2 template, 1 μl of forward primer (10 μM), 1 μl of reverse primer (10 μM), 10 μl of 5*TransStart FastPfu FlyBuffer, 4 μl of 2.5 mM Dntps, 1 μl of TransStart FastPfu Fly DNA Polymerase, 32 μl of ddH$_2$O. The PCR amplification process was 95° C. for 2 min; 32 cycles of 95° C. for 20 s, 55° C. for 20 s, 72° C. for 10 smin; and 72° C. for 5 min.

The *C. glutamicum* H5 genome was used as a template, and the upstream and downstream primers were as follows:

```
ilvAFP:
AAAGGAGGTCATCCACGCTATGAGTGAAACATACGTGTCTGAG ilvARP:
caaaacagccaagctgaattcTTAGGTCAAGTATTCGTACTCAG
```

The DNA fragment ilvA was amplified using TransStart FastPfu Fly DNA Polymerase. The PCR system comprised: 1 μl of genomic template, 1 μl of forward primer (10 μM), 1 μl of reverse primer (10 μM), 10 μl of 5*TransStart FastPfu FlyBuffer, 4 μl of 2.5 mM Dntps, 1 μl of TransStart FastPfu Fly DNA Polymerase, 32 μl of ddH$_2$O. The PCR amplification process was 95° C. for 2 min; 32 cycles of 95° C. for 20 s, 58° C. for 20 s, 72° C. for 30 s; and 72° C. for 5 min.

Plasmid digestion: The plasmid HY-P19 which had been modified by removing the original lacIq and the promoter of PXMJ19 was used. HY-P19 was digested with NEB restriction enzyme XbaI and EcoRI in a 37° C. water bath for 1 h. The amount of plasmid was 1 μg, and 50 μl of enzyme digestion system contained 5 μl plasmid, 1 μl of XbaI, 1 μl of EcoRI, 5 μl of cutsmart, and 38 μl of ddH$_2$O.

DNA recovery by agarose electrophoresis: The PCR products and the digested products were added to a 10*loading buffer, respectively, and 50 μl of which was loaded onto a 1.5% agarose gel. Takara 2000 DL DNA marker was used as a control, and electrophoresis was carried out at 70 V for 40 min. The 160 bp and 1347 bp bands amplified by PCR were recovered according to instruction of the bands of marker. Recovery was carried out using Takara DNA Recovery Kit.

In vitro recombination: In vitro recombination was performed using Vazyme one Step Cloning Kit, and the recombinant products were directly transformed into *E. coli*.

The preparation of E. coli competent cells is the same as that in the construction of promoter probe vectors.

Transformation: competent cells were slowly thawed on ice, 10 μl of the in vitro recombinant products were pipetted into 100 μl of the competent cells, and the centrifuge tube was gently flicked with a finger to mix the cells and recombinant products. The tube was placed in an ice bath or ice water bath for 30 minutes, and then placed in a water bath at 42° C., heating shock for 2 minutes Immediately after heat shock, the centrifuge tube was placed in an ice water bath for 2 minutes. 900 microliters of LB was aliquoted to the tube and the tube was incubated at 37° C. for 200 hours at 200 rpm. The supernatant was removed after centrifugation, and the obtained cells were spread on an LB solid plate containing 25 μg/ml chloramphenicol and cultured at 37° C. overnight.

Transformant verification and plasmid extraction: Transformants that were grown on the resistant plates after transformation were sent to Wuhan Tianyi Huiyuan for sequencing analysis, and transformants with correct sequence were picked and transferred into a tube with 5 ml LB supplemented with a final concentration of 25 μg/ml chloramphenicol. After culturing by shaking at 37° C. and 200 rpm overnight, plasmid was extracted using Takara plasmid kit, and the concentration of the expression plasmid HY-P19-RS10085seq2-ilvA was 269 ng/μl.

2. Construction of the Strain Containing Expression Vector HY-P19-RS10085seq2-ilvA The preparation of electroporation competent Corynebacterium glutamicum cells is the same as that in the construction of promoter probe vectors.

The process of electroporating expression plasmid HY-P19-RS10085seq2-ilvA into host cells Corynebacterium glutamicum H5 is the same as the construction of promoter probe vectors.

The electrotransformed bacterial solution was concentrated by centrifugation, and spread on a LBCIS solid medium supplemented with 10 μg/mL chloramphenicol by a glass rod, and cultured in a 30° C. incubator for 36 hours. The grown transformant was strain with plasmid HY-P19-RS10085seq2-ilvA, which was named H5-RS10085seq2-ilvA.

3. The Fermentation of Strain H5-RS10085seq2-ilvA and Corynebacterium glutamicum H5 to Produce Acid in 5 L Fermenter.

Fermentation medium for the 5 L fermenter: 15 ml/L of corn syrup, 140 g/L of glucose (sterilize alone, moist heat sterilization at 0.075 MPa for 15 min), 5 g/L of ammonium sulfate, 0.4 g/L of potassium dihydrogen phosphate, 0.6 g/L of magnesium sulfate heptahydrate, 0.1 mg/L of biotin, 0.1 mg/L of VB1, 1 ml/L of corn oil, 1 g/L of Angel yeast powder, 1 ml/L of defoamer, moist heat sterilization at 0.01 MPa and 121° C. for 25 min; the initial glucose was then added, and the pH was adjusted to 7.0 with ammonia water.

Culture method: the strain was inoculated into a seed culture medium (seed medium formula: 17 g/L of glucose, 10 ml/L of corn steep liquor, 1 g/L of urea, 0.5 g/L of magnesium sulfate, 1 g/L of dipotassium hydrogen phosphate, 0.1 g/L of yeast paste, 0.1 mg/L of biotin, 10.1 mg/L of vitamin B, 0.1 g/100 ml of corn oil, 1 g/100 ml of calcium carbonate; adjusted pH to 7.0 with NaOH), cultured at 31° C. on a rotary shaker at 200 rpm, for 16 h. After that, the seed culture medium was inoculated to a 5 L automatic control fermenter containing fermentation medium at 10% inoculation amount, and appropriate amount of air was introduced and appropriate stirring speed was set. The dissolved oxygen was controlled by the staged oxygen supply mode: 30% for 0-8$^{th}$ hour, 25% for 8-24$^{th}$ hour, and 12% for 24-56th hour. The pH is controlled at 7.0 by automatic flow of 15% ammonia water, defoaming by fed-batch feeding an appropriate amount of defoamer polyether, and controlling the residual glucose at about 3% by feeding glucose solution with a concentration of 800 g/L. The fermentation ended at 56 h.

After emptying the fermenter, the fermentation broth was detected by HPLC (Ilite C18 column, 5 μm, 4.6*250 mm, and the mobile phase was 0.015 mol/L of diammonium phosphate and 0.005 mol/L of a mixed aqueous solution with pH 7.20. The flow rate was 0.5. ml/min, and the column temperature was 23° C. The detector was an UV detector with a wavelength of 199 nm. The control strain of Corynebacterium glutamicum H5 was fermented and produced 22.0 g/L of acid, 6.3 g/L of heteroacid, and the conversion rate of glucose to acid was 12.83%. The engineering strain H5-RS10085seq2-ilvA was fermented and produced 41.2 g/L of acid, 6.8 g/L of heteroacid, and the conversion rate of glucose to acid was 18.79%.

4. Stability of Plasmid after Fermentation of Strain H5-RS10085seq2-ilvA in a 5 L Fermenter The strains after fermenting for 56 h were diluted to gradient concentrations of $10^{-6}$, $10^{-7}$, $10^{-8}$, and $10^{-9}$ and spread on the plate. 50 μl of strain solution with each concentration was pipetted to spread on chloramphenicol-containing plates and chloramphenicol-free plates, and the plates were then placed in an incubator at 31° C. for 36 h. The loss rate of plasmid was calculated based on the number of colonies growing on the non-resistant plates and the resistant plates. The loss rate of the plasmid=(the number of colonies grown on the chloramphenicol-free plates−the number of colonies grown on the chloramphenicol-containing plates)/the number of colonies grown on the chloramphenicol-free plates×100%. On the plate with $10^{-8}$ dilution gradient, 151 colonies were grown on the chloramphenicol-containing plate, and 167 colonies were grown on the chloramphenicol-free plate. The loss rate of plasmid was only 9.58%, which means the plasmid was stable during fermentation.

Embodiment 3 Expression Vector Constructed Using Promoter Fragment RS07910seq2 and Application Thereof In the process of bacterial metabolism, not all genes can promote the metabolism of target products through their overexpression. Many enzymes produced after gene expression can play a role when they reach a balance point of moderate expression in metabolism. Studies have shown that the global regulatory protein Lrp (which is encoded by the target gene Lrp, and the nucleotide sequence of which is shown in SEQ ID NO: 6) in Corynebacterium glutamicum can increase the transcription level of L-isoleucine synthesis and transportation related genes of Corynebacterium glutamicum, and can also increase the transcription level of the self-encoding gene lrp. However, the overexpression of Lrp inhibits the growth of C. glutamicum. We used the promoter fragment PRS07910seq2 as promoter and lrp as gene of interest to construct the exogenous expression plasmid HY-P19-RS07910seq2-lrp, and the expression plasmid was electrotransformed into Corynebacterium glutamicum H5, an isoleucine-producing strain, to construct a new strain. The acid production capacity of the strain was evaluated by fermentation in a 5 L fermenter.

1. Construction of Expression Vector HY-P19-RS07910seq2-lrp

The screened promoter fragment RS07910seq2 was used as promoter and lrp was used as gene of interest to construct an expression vector HY-P19-RS07910seq2-lrp.

DNA fragment amplification: plasmid PRS07910seq2 was used as a template, and the upstream and downstream primers were as follows:

```
RS07910seq2Fp:
tgcctgcaggtcgactctagaGCGATCACGTAGTCATCCAAG

RS07910seq2Rp:
CACGGTCACGGATGAAGCAT
```

The DNA fragment RS07910seq2 was amplified using TransStart FastPfu Fly DNA Polymerase. The PCR system comprised: 1 μl of P RS07910seq2 template, 1 μl of forward primer (10 μM), 1 μl of reverse primer (10 μM), 10 μl of 5*TransStart FastPfu FlyBuffer, 4 μl of 2.5 mM Dntps, 1 μl of TransStart FastPfu Fly DNA Polymerase, and 32 μl of ddH$_2$O. The PCR amplification process was 95° C. for 2 min, and 32 cycles of 95° C. for 20 s, 55° C. for 20 s, 72° C. for 10 smin with a final 72° C. for 5 min. The C. glutamicum H5 genome was used as a template, and the upstream and downstream primers were as follows:

```
lrpFP: GCTTCATCCGTGACCGTGAtgaagctagattccattgatt lrpRP: caaaacagccaagctgaattctcacacctgggggcgagc
```

The DNA fragment lrp was amplified using TransStart FastPfu Fly DNA Polymerase. The PCR system was as follows: 1 μl of genomic template, 1 μl of forward primer (10 μM), 1 μl of reverse primer (10 μM), 10 μl of 5*TransStart FastPfu FlyBuffer, 4 μl of 2.5 mM Dntps, 1 μl of TransStart FastPfu Fly DNA Polymerase, and 32 μl of ddH$_2$O. The PCR amplification process was 95° C. for 2 min, and 32 cycles of 95° C. for 20 s, 55° C. for 20 s, 72° C. for 10 smin with a final 72° C. for 5 min.

Plasmid digestion: The plasmid HY-P19 modified by removing the original lacIq and the promoter of PXMJ19 was used. HY-P19 was digested with NEB restriction enzyme XbaI and EcoRI in a 37° C. water bath for 1 h, and the amount of plasmid was 1 μg. The 50 μl of enzyme digestion system comprised: 5 μl of plasmid, 1 μl of XbaI, 1 μl of EcoRI, 5 μl of cutsmart, and 38 μl of ddH$_2$O.

The subsequent steps of in vitro recombination, preparation of E. coli competent cells, transformation, and transformant verification and plasmid extraction were the same as those in Embodiment 2, and the finally obtained expression plasmid HY-P19-RS07910seq2-lrp had a concentration of 321 ng/μl.

2. Construction of a Strain Containing the Expression Vector HY-P19-RS07910seq2-lrp The preparation of electroporation competent Corynebacterium glutamicum cells is the same as the construction of the promoter probe vectors.

The electroporation of expression plasmid HY-P19-RS07910seq2-lrp into host cells Corynebacterium glutamicum is the same as the construction of promoter probe vectors.

The electrotransformed bacterial solution was concentrated by centrifugation, and spread on a LBCIS solid medium supplemented with 10 μg/mL chloramphenicol by a glass rod, and cultured in a 30° C. incubator for 36 hours. The grown transformant was exactly the strain with plasmid HY-P19-RS07910seq2-lrp, which was named H5-RS07910seq2-lrp.

3. Strain H5-RS07910seq2-Lrp and Corynebacterium glutamicum H5 were Fermented to Produce Acid in 5 L Fermenter The formulation of the fermentation medium in the 5 L fermenter, the culture method of the strain, and the detection method of the released fermentation broth were the same as those in the embodiment 2, and the results showed that the engineering strain H5-RS07910seq2-lrp produced 39.1 g/L of acid and 6.9. g/L of heteroacid, and the conversion rate of glucose to acid reached 17.88%.

4. Stability of Plasmid after Fermentation of Strain H5-RS07910seq2-Lrp in a 5 L Fermenter The strains after fermenting for 56 h were diluted to gradient concentrations of $10^{-6}$, $10^{-7}$, $10^{-8}$, and $10^{-9}$ and spread on the plate. 50 μl of strain solution with each concentration was pipetted to spread on chloramphenicol-containing plates and chloramphenicol-free plates, and the plates were then placed in an incubator at 31° C. for 36 h. The loss rate of plasmid was calculated based on the number of colonies growing on the non-resistant plates and the resistant plates. The loss rate of the plasmid=(the number of colonies grown on the chloramphenicol-free plates–the number of colonies grown on the chloramphenicol-containing plates)/the number of colonies grown on the chloramphenicol-free plates×100%. On the plate with $10^{-8}$ dilution gradient, 127 colonies were grown on the chloramphenicol-containing plate, and 135 colonies were grown on the chloramphenicol-free plate. The loss rate of plasmid was only 5.93%, which means the plasmid was stable during fermentation.

Embodiment 4 Expression Vector Constructed Using Promoter Fragment RS04670seq2 and Application Thereof In the metabolic process of isoleucine production, 1 mol of isoleucine needs to consume 4 mol of cofactor NADPH. NADPH is mainly derived from the pentose phosphate pathway. The supply of NADPH in organism through this pathway need to consume other metabolites. Changing the carbon flux of the pathway may affect the accumulation of metabolites of interest. By transcriptome analysis, glucose-6-phosphate dehydrogenase in the pentose phosphate pathway is down-regulated in leucine-producing Corynebacterium glutamicum during the stationary phase. Therefore, in order to ensure the supply of the cofactor NADPH in the stationary phase during the metabolic process without affecting the accumulation of the product, the gene gnd of the glucose-6-phosphate dehydrogenase (the sequence is shown in SEQ ID NO: 7) was connected with a promoter to promote the expression of this gene.

1. Construction of Expression Vector HY-P19-RS04670seq2-gnd

The screened promoter fragment RS04670seq2 was used as a promoter and gnd was used as target gene to construct the expression vector HY-P19-RS04670seq2-gnd.

DNA fragment amplification: plasmid PRS04670seq1 was used as a template, and the upstream and downstream primers were as follows:

```
RS04670seq2Fp:
tgcctgcaggtcgactctagaAGGCTGACAGAAACTCTAAAAAC

RS04670seq2Rp:
GGATACCTCCGAAGTTAAGG
```

The DNA fragment RS04670seq1 was amplified using TransStart FastPfu Fly DNA Polymerase. The PCR system comprised: 1 μl of PRS04670seq1 template, 1 μl of forward primer (10 μM), 1 μl of reverse primer (10 μM), 10 μl of 5*TransStart FastPfu FlyBuffer, 4 μl of 2.5 mM Dntps, 1 μl of TransStart FastPfu Fly DNA Polymerase, and 32 μl of ddH$_2$O. The PCR amplification process was 95° C. for 2 min, and 32 cycles of 95° C. for 20 s, 55° C. for 20 s, 72° C. for 10 smin with a final 72° C. for 5 min. The *C. glutamicum* H5 genome was used as a template, and the upstream and downstream primers were as follows:

```
Gnd-FP:
TTAACTTCGGAGGTATCCAtgaagctagattccattgattg gnd-RP:
ccaaaacagccaagctgaattcTTAAGCTTCCACCTCGGAGCG
```

The DNA fragment gnd was amplified using TransStart FastPfu Fly DNA Polymerase. The PCR system comprised 1 μl of genomic template, 1 μl of forward primer (10 μM), 1 μl of reverse primer (10 μM), 10 μl of 5*TransStart FastPfu FlyBuffer, 4 μl of 2.5 mM Dntps, 1 μl of TransStart FastPfu Fly DNA Polymerase, and 32 μl of ddH$_2$O. The PCR amplification process was 95° C. for 2 min, and 32 cycles of 95° C. for 20 s, 55° C. for 20 s, 72° C. for 10 smin with a final 72° C. for 5 min.

Plasmid digestion: The plasmid HY-P19 modified by removing the original lacIq and the promoter of PXMJ19 was used. HY-P19 was digested with NEB restriction enzyme XbaI and EcoRI in a 37° C. water bath for 1 h, and the amount of plasmid was 1 μg. The 50 μl of enzyme digestion system comprised: 5 μl of plasmid, 1 μl of XbaI, 1 μl of EcoRI, 5 μl of cutsmart, and 38 μl of ddH$_2$O.

DNA recovery by agarose electrophoresis: the PCR products and the digested products were added to 10*loading buffer, respectively, and 50 μl of which was loaded onto 3%, 1% agarose gel. Takara 2000 DL DNA marker was used as a control, and electrophoresis was carried out at 70 V for 40 min. The 77 bp and 1481 bp bands amplified by PCR were recovered according to the instruction of the bands of marker. Recovery was carried out using Takara DNA Recovery Kit.

The subsequent steps of in vitro recombination, preparation of *E. coli* competent cells, transformation, and transformant verification and plasmid extraction were the same as in Embodiment 2, and the concentration of the resulting expression plasmid HY-P19-RS04670seq2-gnd was 288 ng/μl.

2. Construction of the Strain Containing the Expression Vector HY-P19-RS04670seq2-gnd The preparation of electroporation competent *Corynebacterium glutamicum* cells is the same as that in the construction of promoter probe vectors.

The process of electroporating expression plasmid HY-P19-RS04670seq2-gnd into host cells *Corynebacterium glutamicum* H5 is the same as the construction of promoter probe vectors.

The electrotransformed bacterial solution was concentrated by centrifugation, and spread on a LBCIS solid medium supplemented with 10 μg/mL chloramphenicol by a glass rod, and cultured in a 30° C. incubator for 36 hours. The grown transformant was exactly the strain with plasmid HY-P19-RS04670seq2-gnd, which was named H5-RS04670seq2-gnd.

3. The Fermentation of Strain H5-RS04670seq2-gnd and *Corynebacterium glutamicum* H5 to Produce Acid in a 5 L Fermenter.

The formulation of the fermentation medium in the 5 L fermenter, the culture method of the strain, and the detection method of the released fermentation broth were the same as those in the embodiment 2, and the results showed that the engineering strain H5-RS04670seq2-gnd produced 33.4 g/L of acid, 7.08 g/L of heteroacid, and the conversion rate of glucose to acid reached 15.31%.

4. Stability of Plasmid after Fermentation of Strain H5-RS04670seq2-gnd in a 5 L Fermenter The strains after fermenting for 56 h were diluted to gradient concentrations of $10^{-6}$, $10^{-7}$, $10^{-8}$, and $10^{-9}$ and spread on the plate. 50 μl of strain solution with each concentration was pipetted to spread on chloramphenicol-containing plates and chloramphenicol-free plates, and the plates were then placed in an incubator at 31° C. for 36 h. The loss rate of plasmid was calculated based on the number of colonies growing on the non-resistant plates and the resistant plates. The loss rate of the plasmid=(the number of colonies grown on the chloramphenicol-free plates–the number of colonies grown on the chloramphenicol-containing plates)/the number of colonies grown on the chloramphenicol-free plates×100%. On the plate with $10^{-8}$ dilution gradient, 118 colonies were grown on the chloramphenicol-containing plate, and 121 colonies were grown on the chloramphenicol-free plate. The loss rate of plasmid was only 2.48%, which means the plasmid was stable during fermentation.

While only specific embodiments of the present invention have been described above, those skilled in the art should understood that these are merely provided for illustration, and many variations or modifications can be made to these embodiments without departing from the principle and spirit of the present invention. Accordingly, the protection scope of the present invention is defined by the appended claims.

SEQUENCE LISTING

This application contains a Sequence Listing which has been submitted electronically in ASCII format and is hereby incorporated by reference in its entirety.
The ASCII text file name is: 14_SQL.txt
Creation date: 11 May 2021
Size: 13,342 bytes.

What is claimed is:

1. A method for screening a *Corynebacterium* constitutive expression vector promoter on the basis of transcriptome sequencing, comprising:

analyzing the transcription level of each gene of the *Corynebacterium* in logarithmic phase and stationary phase, and screening a class of genes with low transcription levels in the logarithmic phase and high transcription levels in the stationary phase are screened by analyzing the transcription abundance of each gene in two phases;

amplifying the promoter fragments of genes and incorporating the DNA fragment of the promoter and marker gene into an expression vector to construct a promoter probe vector;

transforming the probe vector into host cells, and carrying out continuous passage under an antibiotic-stress free condition;

selecting host cells having low expression level of marker gene in the logarithmic phase and high expression level in the stationary phase, and continuously passaged for 50 generations without losing probe vector, thus the promotor transformed by the host cells is the *Corynebacterium* constitutive expression vector promoter comprising a nucleotide sequence of SEQ ID NO: 1, SEQ ID NO: 2 or SEQ ID NO: 3.

2. A *Corynebacterium* constitutive expression vector promoter comprising a nucleotide sequence of SEQ ID NO: 1, SEQ ID NO: 2 or SEQ ID NO: 3.

3. A *Corynebacterium* constitutive expression vector comprising the *Corynebacterium* constitutive expression vector promoter of claim 2.

4. The *Corynebacterium* constitutive expression vector of claim 3, wherein the *Corynebacterium* constitutive expression vector is constructed by inserting a gene of interest and a *Corynebacterium* constitutive expression vector promoter at the restriction site of the plasmid HY-P19, wherein the nucleotide sequence of the plasmid HY-P19 is shown in SEQ ID NO: 4, and the nucleotide sequence of the gene of interest is set forth in SEQ ID NO: 5, SEQ ID NO: 6 or SEQ ID NO: 7.

5. The *Corynebacterium* constitutive expression vector of claim 4, wherein,
the nucleotide sequence of the gene of interest is set forth in SEQ ID NO: 5, provided that the nucleotide sequence of the *Corynebacterium* constitutive expression vector promoter is set forth in SEQ ID NO: 1;
the nucleotide sequence of the gene of interest is set forth in SEQ ID NO: 6, provided that the nucleotide sequence of the *Corynebacterium* constitutive expression vector promoter is set forth in SEQ ID NO: 2; and
the nucleotide sequence of the gene of interest is set forth in SEQ ID NO: 7, provided that the nucleotide sequence of the *Corynebacterium* constitutive expression vector promoter is set forth in SEQ ID NO: 3.

6. A recombinant strain obtained by electroporating the host cells *C. glutamicum* with the expression vector of claim 3.

7. The strain of claim 6, wherein the accession number of the deposited host cells *C. glutamicum* is CCTCC NO: M2016609.

8. A production method, comprising fermenting the recombinant strain of claim 6 in the production of isoleucine.

9. The method of claim 1, wherein the promoter regions of genes that have been screened are analyzed by promotor prediction software, and the promotor regions of said genes are amplified by polymerase chain reaction.

10. The method of claim 1, wherein the method for transforming the probe vector to the host cells is electroporation.

11. The method of claim 1, wherein the OD value (Optical Density value) indicating growth of the host cells is detected by a multifunctional plate reader after the probe vector being transformed into the host cells, and the host cells are cultured to a logarithmic phase and a stationary phase and the expression of the marker gene in two phases is detected, respectively.

12. The method of claim 1, wherein the marker gene is a gene encoding green fluorescent protein.

13. The method of claim 1, wherein host cells which have been selected are the host cells that have been continuously passaged for 50 generations without losing the probe vector.

14. The method of claim 1, wherein the accession number given to *Corynebacterium* is CCTCC NO: M2016609.

15. The method of claim 1, wherein the transcription level of each gene is analyzed by following steps: (1); sample preparation, (2) transcriptome sequencing; and (3) bioinformatics analysis.

16. The method of claim 15, wherein the sample preparation comprises bacteria culturing and RNA extraction, the bacteria is *C. glutamicum*; and/or, the reference species of bioinformatics analysis is *C. glutamicum* ATCC13032.

17. The method of claim 1, wherein low transcription levels in the logarithmic phase and high transcription levels in the stationary phase means that the transcription level in the stationary phase is higher than that in logarithmic phase.

18. The method of claim 17, wherein the transcription level in the stationary phase is 15 times, 45 times, 100 times, 200 times and 300 times higher than that in logarithmic phase.

19. The method of claim 1, wherein the promoter probe vector further comprises a gene encoding green fluorescent protein.

20. The method of claim 1, wherein the initial plasmid used to construct the promoter probe vector is PXMJ19.

* * * * *

SEQUENCE LISTING

<160> NUMBER OF SEQ ID NOS: 7

<210> SEQ ID NO 1
<211> LENGTH: 140

<212> TYPE: DNA
<213> ORGANISM: Corynebacterium glutamicum
<220> FEATURE:
<223> OTHER INFORMATION: RS10085seq2 Promoter

<400> SEQUENCE: 1

```
ctattctata gatctattga aattagtttc tgtaggtcta tagttagagc tggttcaagg     60
ggtgtcaatc ccaaaaggca ctccttgaac tcatgaaaaa gcttgacaaa acttcaacgt    120
caaaggaggt catccacgct                                                140
```

<210> SEQ ID NO 2
<211> LENGTH: 201
<212> TYPE: DNA
<213> ORGANISM: Corynebacterium glutamicum
<220> FEATURE:
<223> OTHER INFORMATION: RS07910seq2 Promoter

<400> SEQUENCE: 2

```
gcgatcacgt agtcatccaa gcaggcgaag aaaccacaat cgtggaccgc gttatcgtca     60
ccaccggcag ctggacaagc gagctcgtgc cctccatcgc gccactgctt gaagtgcgac    120
gcctagtgct cacttggttc ctgcccaaca acccagtgga cttccagccg gaaaatctgc    180
catgcttcat ccgtgaccgt g                                              201
```

<210> SEQ ID NO 3
<211> LENGTH: 207
<212> TYPE: DNA
<213> ORGANISM: Corynebacterium glutamicum
<220> FEATURE:
<223> OTHER INFORMATION: RS04670seq2 Promoter

<400> SEQUENCE: 3

```
gtgggcgctg gccatagtc gccccagctc agcgaagttg tacgccggcg ttgcctgctt      60
gtcgacgttt tttgccactt cccttaattc gggggtggct gaaatgtaag acacgtcact    120
acatttaagc tcaaaaacaa ctacctatag gctgacagaa actctaaaaa ctatagagct    180
atagaaacct aacttcgga ggtatcc                                         207
```

<210> SEQ ID NO 4
<211> LENGTH: 5257
<212> TYPE: DNA
<213> ORGANISM: Artificial Sequence
<220> FEATURE:
<223> OTHER INFORMATION: Plasmid HY-P19

<400> SEQUENCE: 4

```
ggcgcctaac taactaactc gagcttaaga ggcctaagct tgcatgcctg caggtcgact     60
ctagaggatc cccgggtacc gagctcgaat tcagcttggc tgttttggcg gatgagagaa    120
gattttcagc ctgatacaga ttaaatcaga acgcagaagc ggtctgataa aacagaattt    180
gcctggcgga gtagcgcgg tggtcccacc tgacccatg ccgaactcag aagtgaaacg     240
ccgtagcgcc gatggtagtg tggggtctcc ccatgcgaga gtagggaact gccaggcatc    300
aaataaaacg aaaggctcag tcgaaagact gggcctttcg ttttatctgt tgtttgtcgg    360
tgaacgctct cctgagtagg acaaatccgc cgggagcgga tttgaacgtt gcgaagcaac    420
ggcccggagg gtggcgggca ggacgcccgc cataaactgc caggcatcaa attaagcaga    480
aggccatcct gacggatggc cttttgcgt ttctacaaac tcttttgttt attttttctaa    540 atacattcaa atatgtatcc gctcatgaga caataaccct gataaatgct tcaataatat    600
```

```
tgaaaaagga agagtatgag tattcaacat ttccgtgtcg cccttattcc cttttttgcg    660
gcattttgcc ttcctgtttt tgctcaccca gaaacgctgg tgaaagtaaa agatgctgaa    720
gatcagttgg gtgcacgagt gggttacatc gaactggatc tcaacagcgg taagatcctt    780
gagagttttc gccccgaaga acgttttcca atgatgagca cttttgcttc ctcgctcact    840
gactcgctgc gctcggtcgt tcggctgcgg cgagcggtat cagctcactc aaaggcggta    900
atacggttat ccacagaatc aggggataac gcaggaaaga acatgtgagc aaaaggccag    960
caaaaggcca ggaaccgtaa aaaggccgcg ttgctggcgt ttttccatag gctccgcccc   1020
cctgacgagc atcacaaaaa tcgacgctca agtcagaggt ggcgaaaccc gacaggacta   1080
taaagatacc aggcgtttcc ccctggaagc tccctcgtgc gctctcctgt tccgaccctg   1140
ccgcttaccg gatacctgtc cgcctttctc ccttcgggaa gcgtggcgct ttctcaatgc   1200
tcacgctgta ggtatctcag ttcggtgtag tcgttcgct ccaagctggg ctgtgtgcac    1260
gaaccccccg ttcagcccga ccgctgcgcc ttatccggta actatcgtct tgagtccaac   1320
ccggtaagac acgacttatc gccactggca gcagccactg gtaacaggat tagcagagcg   1380
aggtatgtag gcggtgctac agagttcttg aagtggtggc ctaactacgg ctacactaga   1440
aggacagtat ttggtatctg cgctctgctg aagccagtta ccttcggaaa aagagttggt   1500
agctcttgat ccggcaaaca aaccaccgct ggtagcggtg gtttttttgt ttgcaagcag   1560
cagattacgc gcagaaaaaa aggatctcaa gaagatcctt tgatcttttc tacggggtct   1620
gacgctcagt ggaacgaaaa ctcacgttaa gggattttgg tcatgagatt atcaaaaagg   1680
atcttcacct agatcctttt ggggtgggcg aagaactcca gcatgagatc cccgcgctgg   1740
aggatcatcc agccattcgg ggtcgttcac tggttcccct ttctgatttc tggcatagaa   1800 gaaccccgt gaactgtgtg gttccggggg ttgctgattt ttgcgagact tctcgcgcaa    1860
ttccctagct taggtgaaaa caccatgaaa cactagggaa acacccatga acacccatt    1920 agggcagtag ggcggcttct tcgtctaggg cttgcatttg ggcggtgatc tggtctttag   1980
cgtgtgaaag tgtgtcgtag gtggcgtgct caatgcactc gaacgtcacg tcatttaccg   2040
ggtcacggtg ggcaaagaga actagtgggt tagacattgt tttcctcgtt gtcggtggtg   2100
gtgagctttt ctagccgctc ggtaaacgcg gcgatcatga actcttggag gttttcaccg   2160
ttctgcatgc ctgcgcgctt catgtcctca cgtagtgcca aaggaacgcg tgcggtgacc   2220
acgacgggct tagcctttgc ctgcgcttct agtgcttcga tggtggcttg tgcctgcgct   2280
tgctgcgcct gtagtgcctg ttgagcttct tgtagttgct gttctagctg tgccttggtt   2340
gccatgcttt aagactctag tagctttcct gcgatatgtc atgcgcatgc gtagcaaaca   2400
ttgtcctgca actcattcat tatgtgcagt gctcctgtta ctagtcgtac atactctatt   2460
ttacctagtc tgcatgcagt gcatgcacat gcagtcatgt cgtgctaatg tgtaaaacat   2520
gtacatgcag attgctgggg gtgcaggggg cggagccacc ctgtccatgc ggggtgtggg   2580
gcttgccccg ccggtacaga cagtgagcac cggggcacct agtcgcggat acccccccta   2640
ggtatcggac acgtaaccct cccatgtcga tgcaaatctt taacattgag tacgggtaag   2700
ctggcacgca tagccaagct aggcggccac caaacaccac taaaaattaa tagtccctag   2760
acaagacaaa ccccgtgcg agctaccaac tcatatgcac ggggggccaca taacccgaag    2820 gggtttcaat tgacaaccat agcactagct aagacaacgg gcacaacacc cgcacaaact   2880
cgcactgcgc aaccccgcac aacatcgggt ctaggtaaca ctgagtaaca ctgaaataga   2940
agtgaacacc tctaaggaac cgcaggtcaa tgagggttct aaggtcactc gcgctagggc   3000
```

```
gtggcgtagg caaaacgtca tgtacaagat caccaatagt aaggctctgg cggggtgcca   3060
taggtggcgc agggacgaag ctgttgcggt gtcctggtcg tctaacggtg cttcgcagtt   3120
tgagggtctg caaaactctc actctcgctg ggggtcacct ctggctgaat tggaagtcat   3180
gggcgaacgc cgcattgagc tggctattgc tactaagaat cacttggcgg cgggtggcgc   3240
gctcatgatg tttgtgggca ctgttcgaca caaccgctca cagtcatttg cgcaggttga   3300
agcgggtatt aagactgcgt actcttcgat ggtgaaaaca tctcagtgga agaaagaacg   3360
tgcacggtac ggggtggagc acacctatag tgactatgag gtcacagact cttgggcgaa   3420
cggttggcac ttgcaccgca acatgctgtt gttcttggat cgtccactgt ctgacgatga   3480
actcaaggcg tttgaggatt ccatgttttc ccgctggtct gctggtgtgg ttaaggccgg   3540 tatgctgacgcg ccactgcgtg agcacgtggt caaacttgat caggtgtcta cctggggtgg   3600
agacgctgcg aaaatggcaa cctacctcgc taagggcatg tctcaggaac tgactggctc   3660
cgctactaaa accgcgtcta aggggtcgta cacgccgttt cagatgttgg atatgttggc   3720
cgatcaaagc gacgccggcg aggatatgga cgctgttttg gtggctcggt ggcgtgagta   3780
tgaggttggt tctaaaaacc tgcgttcgtc ctggtcacgt ggggctaagc gtgctttggg   3840
cattgattac atagacgctg atgtacgtcg tgaaatggaa gaagaactgt acaagctcgc   3900
cggtctggaa gcaccggaac gggtcgaatc aacccgcgtt gctgttgctt tggtgaagcc   3960
cgatgattgg aaactgattc agtctgattt cgcggttagg cagtacgttc tcgattgcgt   4020
ggataaggct aaggacgtgg ccgctgcgca acgtgtcgct aatgaggtgc tgcaagtct   4080 gggtgtggat tccacccgt gcatgatcgt tatggatgat gtggacttgg acgcggttct   4140
gcctactcat ggggacgcta ctaagcgtga tctgaatgcg gcggtgttcg cgggtaatga   4200
gcagactatt cttcgcaccc actaaaagcg gcataaaccc cgttcgatat tttgtgcgat   4260
gaatttatgg tcaatgtcgc gggggcaaac tatgatgggt cttgttgttg gcgtcccgga   4320
aaacgattcc gaagcccaac cttttcataga aggcggcggt ggaatcgaaa tctcgtgatg   4380
gcaggttggg cgtcgcttgg tcggtcattt cgaagggcac caataactgc cttaaaaaaa   4440
ttacgccccg ccctgccact catcgcagta ctgttgtaat tcattaagca ttctgccgac   4500
atggaagcca tcacagacgg catgatgaac ctgaatcgcc agcggcatca gcaccttgtc   4560
gccttgcgta taatatttgc ccatggtgaa aacggggggcg aagaagttgt ccatattggc   4620
cacgtttaaa tcaaaactgg tgaaactcac ccagggattg gctgagacga aaaacatatt   4680
ctcaataaac cctttaggga aataggccag gttttcaccg taacacgcca catcttgcga   4740
atatatgtgt agaaactgcc ggaaatcgtc gtggtattca ctccagagcg atgaaaacgt   4800
ttcagtttgc tcatggaaaa cggtgtaaca agggtgaaca ctatcccata tcaccagctc   4860
accgtctttc attgccatac ggaactccgg atgagcattc atcaggcggg caagaatgtg   4920
aataaaggcc ggataaaact tgtgcttatt tttctttacg gtcttaaaa aggccgtaat   4980 atccagctga acggtctggt tataggtaca ttgagcaact gactgaaatg cctcaaaatg   5040
ttctttacga tgccattggg atatatcaac ggtggtatat ccagtgattt ttttctccat   5100
tttagcttcc ttagctcctg aaaatctcgt cgaagctcgg cggatttgtc ctactcaagc   5160
tgatccgaca aaatccacac attatcccag gtgtccggat cggtcaaata cgctgccagc   5220
tcatagaccg tatccaaagc atccggggct gatcccc                            5257

<210> SEQ ID NO 5
```

<211> LENGTH: 1311
<212> TYPE: DNA
<213> ORGANISM: Corynebacterium glutamicum
<220> FEATURE:
<223> OTHER INFORMATION: Target gene ilvA

<400> SEQUENCE: 5

| | | | | | |
|---|---|---|---|---|---|
| atgagtgaaa | catacgtgtc | tgagaaaagt | ccaggagtga | tggctagcgg | agcggagctg | 60 |
| attcgtgccg | ccgacattca | aacggcgcag | gcacgaattt | cctccgtcat | tgcaccaact | 120 |
| ccattgcagt | attgccctcg | tctttctgag | gaaaccggag | cggaaatcta | ccttaagcgt | 180 |
| gaggatctgc | aggatgttcg | ttcctacaag | atccgcggtg | cgctgaactc | tggagcgcag | 240 |
| ctcactcagg | agcagcgcga | tgcaggtatc | gttgccgcat | ctgcaggtaa | ccatgcccag | 300 |
| ggcgtggcct | atgtgtgcaa | gtccttgggc | gttcagggac | gcatctatgt | tcctgtgcag | 360 |
| actccaaagc | aaaagcgtga | ccgcatcatg | gttcacggcg | gagagtttgt | ctccttggtg | 420 |
| gtcactggca | taacttcga | cgaagcatcg | gctgcagcgc | atgaagatgc | agagcgcacc | 480 |
| ggcgcaacgc | tgatcgagcc | tttcgatgct | cgcaacaccg | tcatcggtca | gggcaccgtg | 540 |
| gctgctgaga | tcttgtcgca | gctgacttcc | atgggcaaga | gtgcagatca | cgtgatggtt | 600 |
| ccagtcggcg | gtggcggact | tcttgcaggt | gtggtcagct | acatggctga | tatggcacct | 660 |
| cgcactgcga | tcgttggtat | cgaaccagcg | ggagcagcat | ccatgcaggc | tgcattgcac | 720 |
| aatggtggac | caatcacttt | ggagactgtt | gatccctttg | tggacggcgc | agaggtcaaa | 780 |
| cgtgtcggag | atctcaacta | caccatcgtg | gagaagaacc | agggtcgcgt | gcacatgatg | 840 |
| agcgcgaccg | agggcgctgt | gtgtactgag | atgctcgatc | tttaccaaaa | cgaaggcatc | 900 |
| atcgcggagc | ctgctggcgc | gctgtctatc | gctgggttga | aggaaatgtc | ctttgcacct | 960 |
| ggttctgtcg | cggtgtgcat | catctctggt | ggcaacaacg | atgtgctgcg | ttatgcggaa | 1020 |
| atcgctgagc | gctccttggt | gcaccgcggt | ttgaagcact | acttcttggt | gaacttcccg | 1080 |
| caaaagcctg | gtcagttgcg | tcacttcctg | gaagatatcc | tgggaccgga | tgatgacatc | 1140 |
| acgctgtttg | agtacctcaa | gcgcaacaac | cgtgagaccg | gtactgcgtt | ggtgggtatt | 1200 |
| cacttgagtg | aagcatcagg | attggattct | ttgctggaac | gtatggagga | atcggcaatt | 1260 |
| gattcccgtc | gcctcgagcc | gggcacccct | gagtacgaat | acttgacctra | | 1311 |

<210> SEQ ID NO 6
<211> LENGTH: 456
<212> TYPE: DNA
<213> ORGANISM: Corynebacterium glutamicum
<220> FEATURE:
<223> OTHER INFORMATION: Target gene Lrp

<400> SEQUENCE: 6

| | | | | | |
|---|---|---|---|---|---|
| atgaagctag | attccattga | ttgcgcaatt | attgcggagc | ttagcgcgaa | tgcgcgcatc | 60 |
| tcaaatctcg | cactggctga | caaggtgcat | ctcactccgg | gaccttgctt | gaggagggtg | 120 |
| cagcgtttgg | aagccgaagg | aatcattttg | ggctacagcg | cggacattca | ccctgcggtg | 180 |
| atgaatcgtg | gatttgaggt | gaccgtggat | gtcactctca | gcaacttcga | ccgctccact | 240 |
| gtagacaatt | ttgaaagctc | cgttgcgcag | catgatgaag | tactggagtt | gcacaggctt | 300 |
| tttggttcgc | cagattattt | tgttcgcatc | ggcgttgctg | atttggaggc | gtatgagcaa | 360 |
| ttttatcca | gtcacattca | aaccgtgcca | ggaattgcaa | agatctcatc | acgttttgct | 420 |
| atgaaagtgg | tgaaaccagc | tcgccccag | gtgtga | | | 456 |

```
<210> SEQ ID NO 7
<211> LENGTH: 1455
<212> TYPE: DNA
<213> ORGANISM: Corynebacterium glutamicum
<220> FEATURE:
<223> OTHER INFORMATION: Target gene gnd

<400> SEQUENCE: 7
atgactaatg gagataatct cgcacagatc ggcgttgtag gcctagcagt aatgcgctca      60
aacctcgccc gcaacttcgc ccgcaacggc aacactgtcg ctgtctacaa ccgcagcact     120
gacaaaaccg acaagctcat cgccgatcac ggctccgaag gcaccttcat cccttccgca     180
accgtcgaag agttcgtagc atccctggaa aagccacgcc gcgccatcat catggttcag     240
gctggtaacg ccaccgacgc agtcatcaac cagctagcag atgccatgga cgaaggcgac     300
atcatcatcg acggcggcaa cgtcctctac accgacacca ttcgtcgcga gaaggaaatc     360
tacgcacgcg gtctccactt cgtcggtgct ggtatctccg gcggccaaga aggcgcactc     420 aacgcccat ccatcatgcc tggtggccca gcaaagtcct acgagtccct cggaccactg      480
cttgaatcca tcgctgccaa cgttgacggc acatcatgtg tcacccacat cggaacagac     540
ggcgccggcc acttcgtcaa gatggtccac aacggcatcg agtacgcgga catgcaggtc     600
atcggcgagg cataccacct tctccgctac gcagcaggca tgcagccagc tgaaatcgct     660
gaggaattca aggaatggaa cgcaggcgac ctggattcct acctcatcga aatcaccgca     720
gaggttctct cccaggtgga tgctggaacc ggcaagccac tgatcgacgt catcgttgac     780
gctgcaggcc agaagggcac cggacgttgg accgtcaagg ctgctcttga tctgggtatt     840
gctaccaccg gcatcggcga agctgttttc gcacgtgcac tctccggcgc aaccagccag     900
cgcgctgcag cacagggcaa cctacctgca ggtgtcctca ccgatctgga agcacttggc     960
atggacaagg cacagttcgt cgaagacgtt cgttgtgcac tgtacgcatc caagcttgtt    1020
gcttacgcac agggcttcga cgagatcaag gctggctccg acgagaacaa ctgggacgtt    1080
gaccctcgcg acctcgctac catctggcgc ggcggctgca tcattcgcgc taagttcctc    1140
aaccgcatcg tcgaagcata cgatgcaaac gctgaacttg agtccctgct gctcgatcct    1200
tacttcaaga gcgagctcgg cgacctcatc gattcatggc gtcgcgtgat tgtcaccgcc    1260
acccagcttg gcctgccaat cccagtgttc gcttcctccc tgtcctacta cgacagcctg    1320
cgtgcagagc gtctgccagc agccctgatc cagggacagc gcgacttctt cggtgcgcac    1380
acctacaagc gcatcgacaa ggatggctcc ttccacaccg agtggtccgg cgaccgctcc    1440
gaggtggtag cttaa                                                    1455
```